United States Patent [19]
Hartzell et al.

[11] Patent Number: 4,949,726
[45] Date of Patent: Aug. 21, 1990

[54] BRAINWAVE-RESPONSIVE APPARATUS

[75] Inventors: Rex Hartzell; E. Dale Walters, both of Topeka, Kans.; Julian Gresser, Sausalito, Calif.

[73] Assignee: Discovery Engineering International, Sausalito, Calif.

[21] Appl. No.: 174,784

[22] Filed: Mar. 29, 1988

[51] Int. Cl.$^5$ ............................................. A61B 5/04
[52] U.S. Cl. ..................................... 128/731; 273/1 E
[58] Field of Search ................... 273/1 E, DIG. 28; 128/731, 732

[56] References Cited

U.S. PATENT DOCUMENTS

| | | | |
|---|---|---|---|
| 3,855,998 | 12/1974 | Hidalgo-Briceno | 273/1 E X |
| 4,013,068 | 3/1977 | Settle et al. | 128/419 R X |
| 4,126,125 | 11/1978 | Agoston | 128/732 |
| 4,140,997 | 2/1979 | Brady | 128/732 |
| 4,149,716 | 4/1979 | Scudder | 273/DIG. 28 X |

Primary Examiner—Francis Jaworski
Attorney, Agent, or Firm—Fliesler, Dubb Meyer & Lovejoy

[57] ABSTRACT

Apparatus is disclosed for use with one or more subjects simultaneously, for causing an output device to perform productive functions, such as various types of movement of an object, in response to the subject's movement between various brainwave states and combinations of brainwave states. When more than one subject is involved, the apparatus can generate an output signal indicating when all the subjects are producing a predetermined brainwave pattern simultaneously, when they are producing a predetermined brainwave pattern synchronously; when they producing a predetermined brainwave pattern coherently; or when, during a preceding predetermined interval of time, each of the subjects individually produced a predetermined brainwave pattern for more than a predetermined percentage of the interval of time.

31 Claims, 8 Drawing Sheets

BRAINWAVE-RESPONSIVE APPARATUS

BACKGROUND OF THE INVENTION

1. Field of the Invention

The invention relates to the use of brainwave-responsive apparatus for controlling productive functions, such as movement, and more particularly to the use of such apparatus in response to the presence and amplitude of non-alpha brainwaves and various combinations of brainwaves. The invention further relates to extensions of these techniques for use with more than one subject in combination.

2. Description of Related Art

A. Brainwaves

It is well known that the human brain generates electrical impulses which may be sensed by probes placed outside the head. These signals are believed to be generated from neuronal firings under the probes, and various patterns of brainwave rhythm can be observed. If the cells fire synchronously, generally higher amplitudes are observed.

It has been found that the different brainwave patterns which are observed in humans can be categorized depending on whether the brainwave includes frequency components in four specific frequency bands. The definitions of these bands have been developed to coincide with four corresponding grossly different states of consciousness. The bands are as follows:

Beta (13 to 26 hertz). A person exhibiting beta waves is usually awake, alert, attending to external stimuli, thinking, active, focussing outside himself, doing analytic problem solving, being apprehensive or being anxious. Beta waves are prevalent when a person is looking at and listening to a speaker or a television program.

Alpha (8 to 13 hertz). A person exhibiting alpha waves is usually awake, consciously aware, receptive, relaxed, not attending to external stimuli, and focussed internally. Most individuals produce alpha when they close their eyes and their bodies are relaxed, but it is possible to produce alpha even when one's eyes are open. It is a nothing-in-particular, reflective state which often takes over when an individual closes his eyes while listening to a speaker he finds boring.

Theta (4 to 8 hertz). A drowsy or near-unconscious state, in which one is focussed internally, detached from incoming information. The theta state often appears just before and after sleep, and is frequently accompanied by hypnagogic and dream-like images. Like alpha, however, it is possible, through training, to produce occipital lobe theta waves while being alert and attending to the outside world. Recent work suggests that it may be highly beneficial to be able to enter a theta state volitionally since the hypnogogic images which are produced can sometimes be used for enhanced creativity or for diagnosing physiological or psychological disorders of the subject. For example, see Green, Green & Walters, *Brainwave Training, Imagery, Creativity and Integrative Experiences* (paper presented at the Biofeedback Research Society Conference, Feb., 1974). See also Green and Green, *Biofeedback and States of Consciousness*, Chapter 18 of Wolman and Ullman, *Handbook of States of Consciousness* (new York: VanNostrand Reinhold, 1986).

Delta (0.5 to 4 hertz). Deep, dreamless, non-REM sleep.

The above frequency definitions for the alpha, beta, theta and delta bands are only approximate and will vary from individual to individual. Some research papers have defined these bands slightly differently. Since these definitions seem to coincide well with the four states of consciousness described above in a majority of the population, however, these are the definitions which will be assumed for purposes of illustration herein. It will be understood that other, slightly different, definitions could also be used.

B. Brainwave-Responsive Apparatus

Various kinds of devices have been constructed in the past for sensing brainwave potentials. In the simplest form, the brainwave potentials are detected and plotted on a graph-type strip chart recorder. Other devices have been constructed to sense the brainwave potentials and to utilize the sensed potentials or portions thereof for providing certain feedback indications.

Most electroencephalographic (EEG) responsive apparatus available today, other than strip chart recorders, are designed to provide feedback indicating whether the subject is "in an alpha state, beta state, theta state or delta state. An individual can produce brainwaves in more than one of the frequency bands at the same time, however, and some devices have been developed which provide simultaneous feedback concerning more than one band. All such devices merely provide the feedback indicative of one band at the same time they provide the feedback indicative of the other band. In tone feedback, for example, two tones will be on at once.

In U.S. Pat. No. 3,821,949 to Hartzell, Green, et al., biofeedback potentials are processed through separate parallel processing channels of a controlling channel, each processing channel processing a preselected frequency range of the selected brainwave potential to provide subject-perceivable feedback signals indicative of signal presence within the preselected frequency of the processing channel. Each processing channel is constructed to provide predetermined signal amplitude and duration criteria for determining signal presence prior to initiating and terminating the feedback signals. According to the disclosure of that patent, each processing channel may be constructed to provide feedback signals indicative of the percentage of time during a subsequent predetermined epoch of time wherein a signal presence existed in the sensed brainwave potential. Also according to the disclosure, the biofeedback apparatus simultaneously produces audible feedback signals, each audible feedback signal having a separately identifiable tone indicative of signal presence within the preselected frequency range of the processing channels. A variation on the basic apparatus is disclosed in which two separate pickups, preferably for placement at the left and right occipital lobes, are processed to provide separate feedback signals to left and right speakers of a stereo headset. A switch is also provided for combining the two audio signals to provide a monaural signal to both speakers.

Another device, manufactured by J & J Enterprises, Poulsbo, Washington, is an input device which may be used with a personal computer. It provides inputs and corresponding probes for sensing temperature, EMG signals, respiration, EKG signals, blood volume pulses and brainwave signals. Software is provided whereby a user may obtain visual and/or audio feedback of these signals.

Other brainwave-responsive apparatus is known in which some productive function is performed, for example, operating a toy helicopter. However, brainwave-responsive apparatus performing productive functions (as opposed to merely providing informational feedback or recording and analysis functions) have been limited in their responsiveness to the presence or absence of alpha waves only. Apparatus performing a productive function in response to theta waves has not been considered, presumably because it has generally been assumed that the voluntary movement into a theta phase by a subject is unreliable.

Various other brainwave-responsive devices are typified in U.S. Pats. Nos.: 3,548,812 to Paine; 3,032,029 to Cunningham; 3,195,533 to Fischer; 2,860,627 to Harden; 2,848,992 to Pigeon; and 3,513,834 to Suzuki. These patents are discussed in the aforementioned Hartzell patent.

SUMMARY OF THE INVENTION

It is therefore an object of the present invention to provide brainwave-responsive apparatus not subject to the limitations of the foregoing apparatus.

It is another object of the present invention to provide brainwave-responsive apparatus for performing a productive function in response to the presence or absence of beta or theta waves.

It is another object of the present invention to provide brainwave-responsive apparatus for performing different productive functions in response to different predetermined brainwave patterns and combinations thereof being produced by a single subject.

It is another object of the present invention to provide empathy training apparatus, whereby two or more subjects may be trained to produce theta waves, either simultaneously, synchronously or coherently.

It is another object of the present invention to provide beta brainwave training apparatus for elderly subjects.

It is another object of the present invention to provide apparatus for controlling different functions of a toy vehicle in response to brainwave patterns of a subject, preferably a child.

The above objects and others may be achieved according to the invention by providing one or more brainwave detection units depending on the number of subjects involved. Each such detection unit may have a beta, an alpha and a theta presence output, indicating the presence or absence of brainwaves in the corresponding frequency ranges in the subject, and may further have respective beta, alpha and theta amplitude outputs. Device control apparatus is also provided which causes an output device, such as a toy vehicle, to perform some productive function, such as moving forward, moving backward, turning left or turning right, depending on the state of the various presence outputs for a single one of the subjects. The device control apparatus may also cause the output device to perform productive functions in response to the simultaneous presence in the subject of exactly a predetermined pair of the brainwave signals, the simultaneous presence of brainwaves in all three frequency ranges, or the simultaneous absence of brainwaves in all three of the frequency ranges.

In another aspect of the invention, apparatus is provided for providing to a plurality of subjects a combined informational feedback signal which is indicative either of their simultaneous production of brainwaves within a predetermined band, such as theta; the production of synchronous brainwave patterns produced by the different subjects, with out without coherence; or the production by all subjects within the previous predetermined interval of time of a predetermined brainwave pattern, such as theta waves, for at least a predetermined percentage of the interval of time. This combined feedback may be provided instead of or in addition to individualized feedback to each of the subjects.

In another aspect of the invention, device control apparatus is provided for causing an output device to perform a productive function in response to the combined signals of a plurality of subjects as described above. The apparatus may or may not include feedback to the subjects.

BRIEF DESCRIPTION OF THE DRAWINGS

The invention will be described with respect to specific embodiments thereof. Other objects, embodiments and features of the invention will be apparent from a reading of the detailed description in conjunction with the drawings, in which.

DETAILED DESCRIPTION

Figure 1:
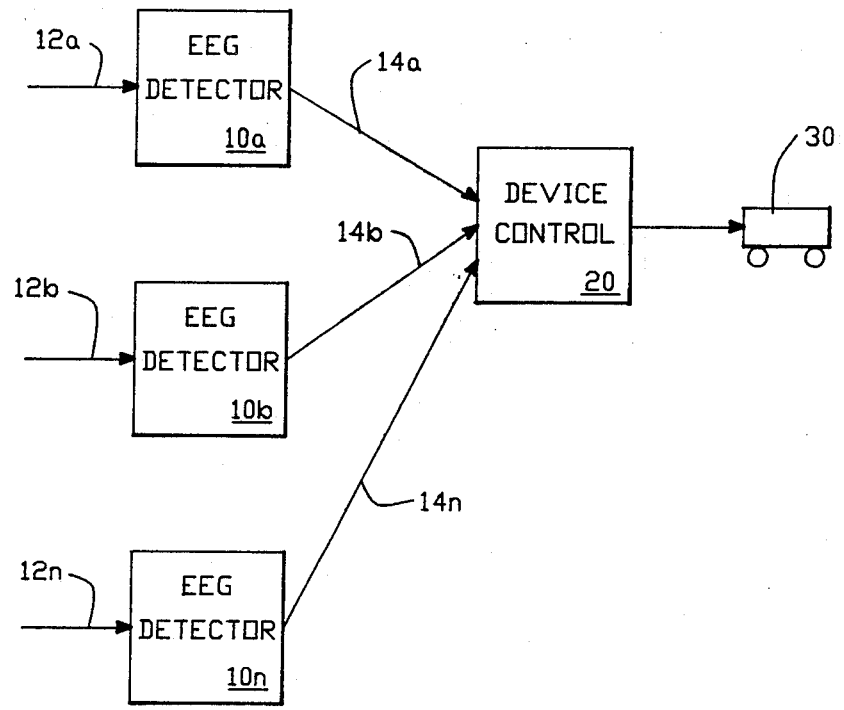
FIG. 1 is a block diagram of apparatus incorporating the invention.

FIG. 1 shows a block diagram of apparatus incorporating the present invention. It will be understood that the distribution of functions represented by the block diagram is only illustrative, and a different distribution, such as combining functions of more than one block into one, is equally possible. The apparatus consists of one or more EEG detectors $10a$–$10n$, each having input lines $12a$–$12n$ and output lines $14a$–$14n$. The input lines $12a$ are connected to pickups for connection to one subject. When the apparatus is used to detect empathetic brainwave signals among two or more subjects, the input lines $12b$–$12n$ are also used for connection to the different subjects being monitored for empathetic response.

Each of the detectors $10a$–$10n$ generates various signals on its outputs $14a$–$14n$, respectively, which are processed by device control apparatus 20 in a manner described hereinafter. Device control apparatus 20 either provides signals for controlling, or actually controls, some output device 30. The output device 30 is shown in FIG. 1 illustratively as a toy vehicle.

Each of the EEG detectors $10a$–$10n$ may be constructed according to the aforementioned Hartzell patent. That patent is incorporated herein by reference in its entirety, and the circuitry described therein will not be repeated here. Several aspects of the device should, however, be pointed out.

First, it should be noted that the EEG detector $10a$ may have the following outputs: beta, alpha and theta presence (digital signals indicative respectively of the presence or absence of brainwave signals in the beta, alpha and theta bands); beta, alpha and theta amplitude (analog signals indicative of the amplitude of the subject's brainwaves in, respectively, the beta, alpha and theta bands); beta, alpha and theta filter outputs (carrying an amplified version of the subject's brainwaves as they appear after passing through respective beta, alpha and theta bandpass filters); and raw EEG (an amplified version of the subject's brainwaves, unfiltered). Depending on the application, some or all of these outputs will be present in EEG detectors 10a-10n. For flexibility and illustration, it is assumed herein that all such outputs are available and supplied on lines 14a-14n.

Second, though the input lines 12a-12n are described in the Hartzell patent as being connected to electrodes for attachment to the scalp of the subject, it will be understood that other pickup devices, such as SQUIDs, may be substituted.

Third, the Hartzell apparatus permits a user to adjust his threshold individually for each of the three bands. For example, beta, alpha and theta thresholds each may be adjusted continuously between 5 and 150 microvolts. A subject exhibiting EEG signals within a given one of the three bands with an amplitude below the preset threshold is not considered by the equipment to have brainwaves present in that band.

Fourth, the Hartzell EEG detection apparatus employs hysteresis circuitry in the determination of whether the subject is producing brainwaves within a given band. Brainwave signals are rarely clean, and frequently exhibit individual cycles or one and one-half cycle intervals which have a period corresponding to frequencies within different ones of the bands. Since these events do not indicate any significant physiological process, or any real change in the subject's state of consciousness, they should be ignored. Thus the apparatus does not indicate the presence of brainwaves within any of the three bands until the subject exhibits brainwaves within that band which have an amplitude above the threshold value for a time period equivalent to about 3 cycles at the mid-band frequency. For example, since the definition of the theta band is 4 to 8 hertz, the mid-band frequency for theta is 6 hertz. The subject would have to exhibit brainwaves above the threshold within the theta range for at least $1/6 = 0.51$ seconds before the theta presence output of the EEG detector 10a would become active. Similarly, the presence indication does not become inactive until the subject fails to produce brainwaves above the threshold, continuously for a period equivalent to about 3 cycles at the mid-band frequency.

Finally, the EEG detector 10a incorporates an artifact inhibit circuit with a variable threshold. An artifact is a Bignal picked up from a source different from the subject's brainwaves. Typically, these come from EMG signals caused by head movements, eye blinks or jaw clenching. The apparatus inhibits artifacts by inhibiting all output when the input rises above a certain predetermined amplitude threshold which is significantly higher than the thresholds set for the beta, alpha and theta bands.

Figure 2A:
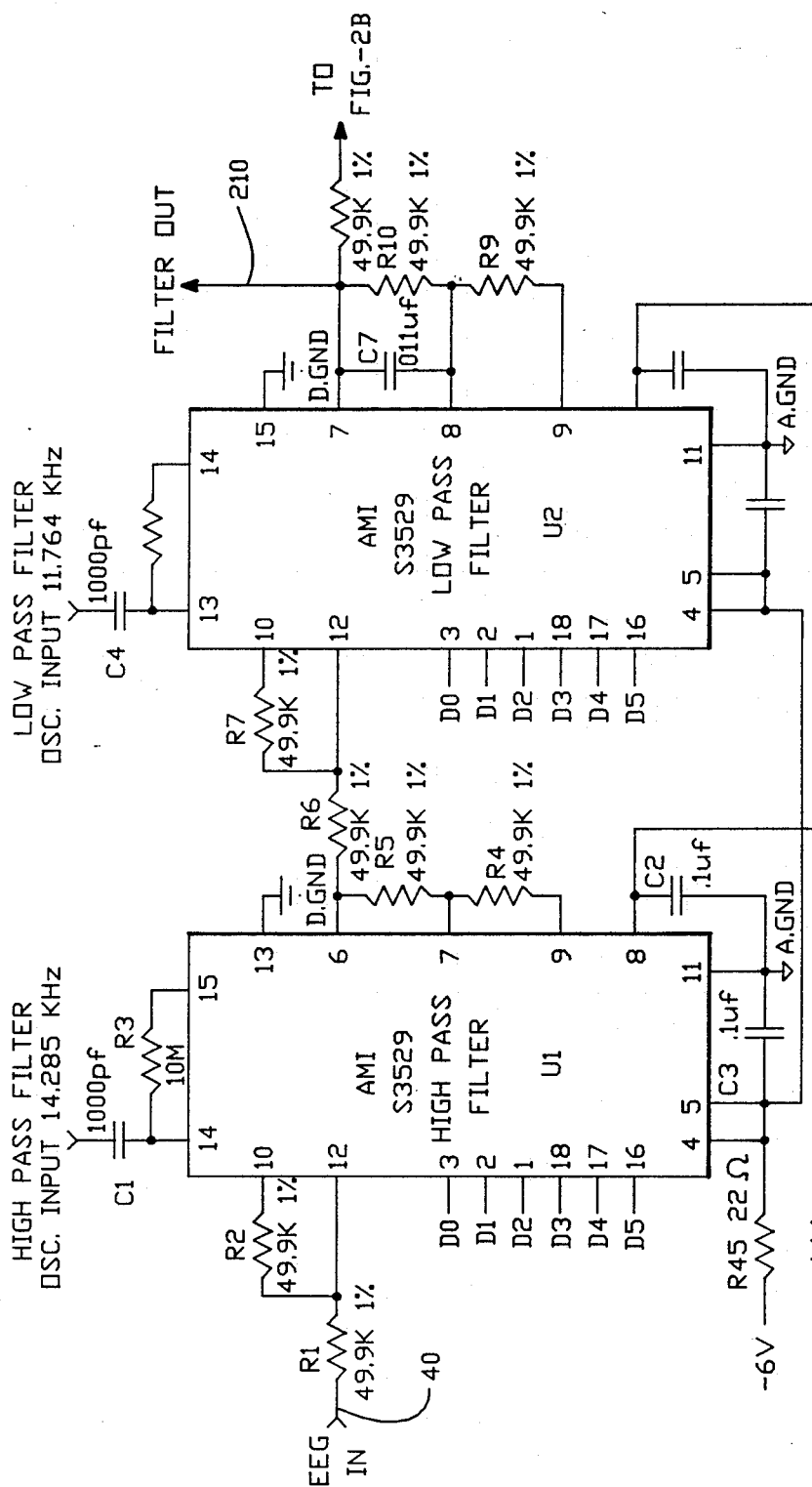
FIG. 2 is a schematic diagram of an EEG detector as shown in FIG. 1.
Figure 2B:
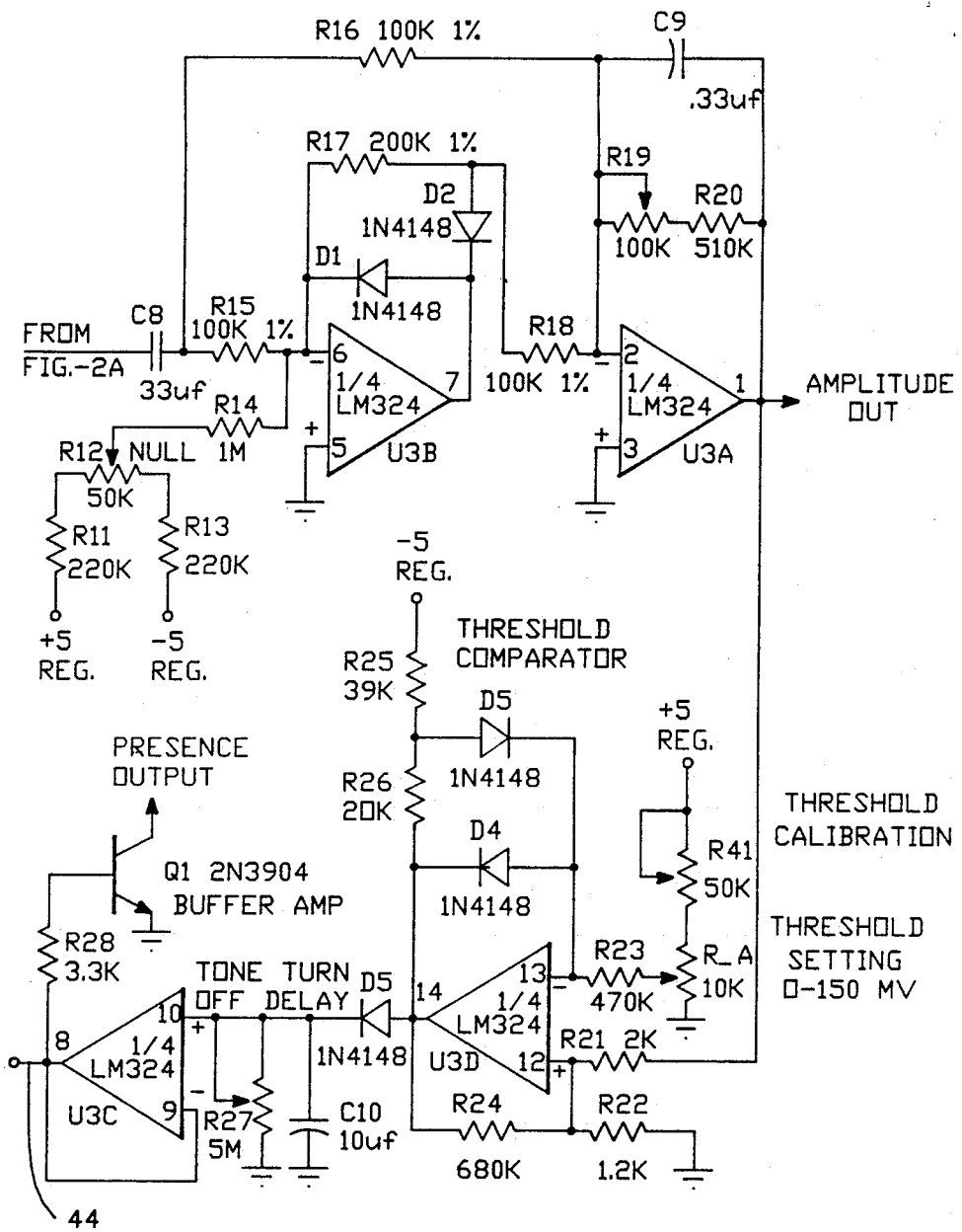

Analog processing technology has improved and miniatured substantially since the filing of the Hartzell patent, and the person of ordinary skill will understand how to update the circuitry For guidance, FIG. 2 shows a schematic diagram of updated circuitry for processing any one of the three bands. The filter chips $U_1$ and $U_2$ each have a 6-bit digital input, and input signals according to Table 42 in FIG. 2 may be applied to these inputs in order to adapt the circuit of FIG. 2 for use either in beta, alpha or theta detection. The input 40 of the circuit derives from the output of a preamplifier (not shown), the input of which receives the pickup signals. Finally, all the outputs (presence, etc.) associated with the channel selected by the filter digital inputs are indicated on the drawing. An additional output line 44 may be used for controlling other circuitry, such as an audible tone output as described in Hartzell. The remainder of FIG. 2 is self explanatory to a person of ordinary skill.

EEG detectors 10a-10n are each designed to generate output signals corresponding to all three of the bands (beta, alpha and theta) as defined above. As previously explained, it is advantageous to use these bands because they coincide with different gross states of consciousness. It is easier to train a subject to move in and out of these bands than it is to train the subject to exhibit some other brainwave pattern, since it is more likely that the subject will be able to detect and recognize internally when he is in one of these bands. A subject will therefore find it easier to train himself to produce beta, alpha or theta than to produce some other brainwave pattern, such as a signal between 7-12 hertz.

It is also more useful to train subjects to enter these states for therapeutic reasons. For the elderly, for example, beta training would improve concentration and attention. For children, theta training would help reduce hyperactivity.

In an important use of the invention, theta training is also known to promote hypnagogic imagery and other techniques associated with self-healing. In this connection, theta training apparatus may be used as an integral part of a method for discovering solutions to problems. Theta training tends to help a subject sharpen his visualization of a "master" for solving a problem, helps boost one's energy to the higher state required to enhance creativity, enhances dream incubation, helps in the identification of external sources of feedback and helps increase the subject's awareness of things going on around him. All these effects are useful in such a method of discovery. Moreover, work on prior art theta training apparatus shows that these benefits appear to arise not only while a subject is in theta, but also merely by reason of his having worked with a theta trainer.

Theta training devices may also be used to monitor a subject's discovery potential, since the theta threshold level which he has reached in his training appears to be an indicator of his discovery potential.

A device incorporating an EEG detector such as 10a may be operated as follows. The pickups or electrodes are first placed on the subject's scalp in accordance with standard procedures. A good choice for initial electrode placement is the left occipital ($O_1$) area referenced to the left ear ($A_1$) with the ground electrode on the right ear ($A_2$), in accordance with the International 10-20 system of EEG electrode placement. Use of the left occipital region is advantageous since this part of the brain is most closely associated with vision. It tends to be the quickest area to move from beta to alpha, which is usuallY, but not always, the first step toward moving to theta. See Banquet, "Spectral Analysis of the EEG in Meditation," *Electroencephalography and Clinical Neurophysiology*, Vol. 35, pp 143-51 (1973).

Once the probes are placed on the subject's scalp, the various thresholds are set to initial values as follows. First, the alpha band threshold is set to the minimum level. Some means are provided, such as a speaker emitting a tone, for feeding back to the subject an indication of whether or not the subject is producing brainwaves in the alpha range. According to standard procedure, the subject closes his eyes and relaxes, thinking of nothing specific, letting his mind go blank. When the tone comes on, the threshold is increased until the tone ceases and then decreased until the tone is heard about 40-60% of the time.

The theta threshold is set initially to approximately ¾ of the level of the alpha threshold. In order to set the beta threshold, the subject sits with eyes open, thinking on a specific topic. The threshold adjustment is then increased from a low level until the beta feedback tone ceases. The microvolt setting at which this occurs is noted, and the threshold is set at 60% of that reading. The artifact inhibit threshold is set at 2.5 times the microvolt setting of the highest threshold setting.

Assuming some informational feedback is provided, such as tones indicating the presence or absence of EEG signals in each of the three bands as described in the Hartzell patent, the subject is now part of a closed-loop feedback system. By monitoring the feedback and the corresponding mental state, a subject can learn to regulate small shifts in feelings and attention and thereby gradually learn to enhance or suppress EEG frequencies or amplitude. It has been observed and it is well known that subjects can, using the equipment such as that described in the Hartzell patent, learn to volitionally move from one brainwave state to another, merely by self-monitoring by the subject of his own mental state, feelings and attention level, eventually without the aid of informational feedback.

Since the subject should be relaxed as much as possible (but not asleep) while practicing brainwave biofeedback, various relaxation techniques may prove helpful. Good descriptions of certain of these techniques may be found in Jacobson, E., "Progressive Relaxation" or in Luthe, W., "Autogenic Therapy."

Before describing the device control apparatus 20, it is useful to define some categories of functions which may be performed by output device 30. Most commonly in the past, the only output provided by an EEG detector such as 10a has been either in the form of tones or lights observable by the subject, or in the form of recording apparatus such as strip chart recorders or magnetic tape. The only purpose of such an output device is either for providing informational feedback to the subject, to better enable the subject to control his brainwave pattern, or for recording and analysis. Sometimes both types of outputs, solely informational and solely recording and analysis, are provided. Very few output devices perform productive functions, such as controlling movement of an output device. Those units which are known and which do perform a productive function, such as the toy helicopter control apparatus described above, perform such function only in response to the presence or absence of alpha waves.

It should be noted that an output device performing a productive function may well be observable by the subject and thereby provide informational feedback as well. An output device performing a recording function, such as a strip chart recorder, may also provide informational feedback, for example if the subject is looking at it. The productive and recording functions, however, may be provided without also providing informational feedback to the subject, as by placing the output device in another room.

As an aside, it may be noted that according to a related invention, feedback may be provided to a subject not in the form of fixed tones, but in some form which itself helps to reinforce the state of consciousness corresponding to the brainwave pattern sought. For example, if the subject seeks to enter a theta state, a soothing, familiar music may be started when theta appears and stopped when it fades away. If the subject seeks a beta state, feedback may be in the form of the sound output from a television console playing the subject's favorite program.

Figure 3:
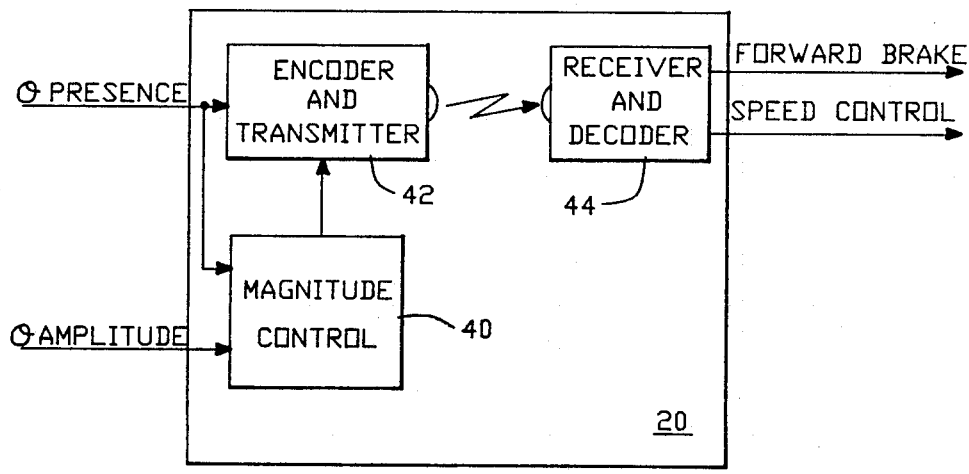
FIGS. 3 and 5-9 show block diagrams of various embodiments of the device control block and output device shoWn in FIG. 1.

FIG. 3 shows a simplified structure which may be used for device control block 20 in FIG. 1. In the form shown, this apparatus is intended for use with a single subject hooked up to only one of the EEG detectors 10a-10n. For the purposes of this illustration, the subject is intended to be a child, since children are more frequently in a theta state than are adults. And since the subject is a child, the output device 30 is assumed to be a toy vehicle capable of braking or of moving forward at a selected speed, both by remote control.

The device control block 20 in FIG. 3 comprises a magnitude control block 40 receiving as inputs the theta presence and amplitude outputs of EEG detector 10a. The output of magnitude control block 40 forms an input to encoder/transmitter 42, as does the theta presence output of EEG detector 10a. The encoder/transmitter 42 encodes the input signals and transmits them via infrared radiation to a receiver/decoder 44, which decodes the signal and generates a forward/brake signal and a speed-control signal for the toy vehicle 30. It should be noted that though infrared transmission is used for remote control of the output device in FIG. 3, radio transmission will also suffice. Additionally, encoding and decoding of the theta presence and theta amplitude signals may not be necessary at all if these signals are transmitted along wires directly to the toy vehicle.

Figure 4:
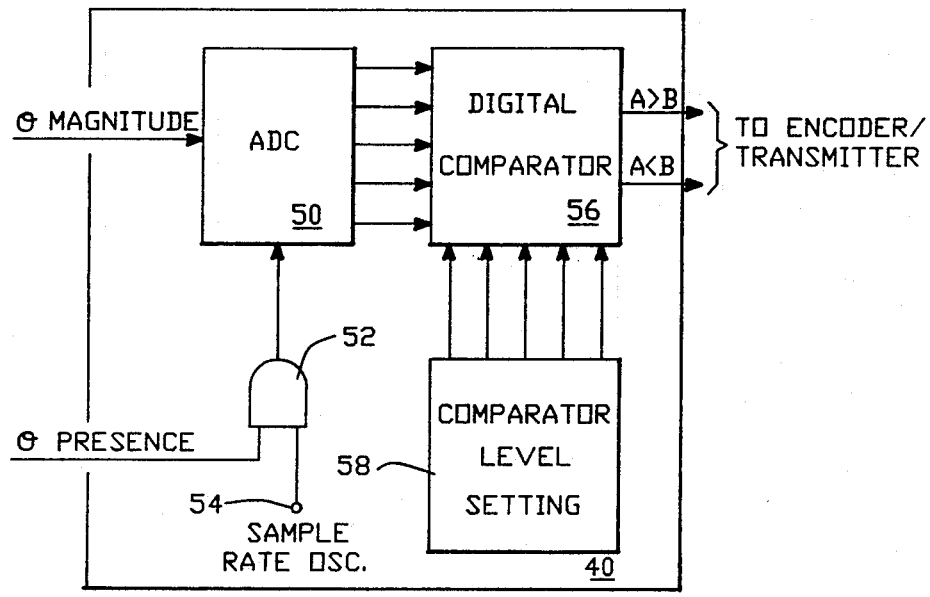
FIG. 4 shows a block diagram of a magnitude control block shown in FIGS. 3, 6 and 7.

The construction of the magnitude control block 40, the encoder/transmitter 42 and the receiver/decoder 44 is conventional. Typical apparatus for performing the magnitude control function of block 40 is shown in FIG. 4. It comprises an analog-to-digital converter (ADC) 50 having its analog input connected to the theta magnitude output of EEG detector 10a. The sample clock input of the ADC 50 is connected to the output of an AND gate 52, the two inputs of which are connected, respectively, to the theta presence output of the EEG detector 10a and a sample rate oscillator 54. The digital outputs of ADC 50 connect to an A input of a digital comparator 56, the B input of which is connected to the output of a comparator level setting circuit 58 which may be hard-wired jumpers or a dip switch. The digital comparator 56 forms two outputs: an A<B output and an A>B output, which are digital signals sent to encoder/transmitter 42.

In operation, the apparatus of FIGS. 1, 2 and 3 operates to control the motion of a toy vehicle 30 in response to the presence, absence and magnitude of a child's theta waves. As previously noted, prior art devices which controlled productive functions did so only in response to alpha waves. As shown in the drawings, the vehicle 30 will move forward when the child is producing theta waves, at a speed which is determined by the amplitude of the child's theta waves. Only two forward speeds are generated by the apparatus, with an amplitude threshold setting determined by the comparator level setting block 58. It will be understood, however, that any number of speed settings are possible. Additionally, the vehicle will brake when the child stops producing theta with an amplitude greater than the theta threshold setting of the EEG detector 10a.

It should be noted that if the subject can see the vehicle, the productive function accomplished by its motion and/or braking also provides informational feedback to help the subject know when theta waves are being produced and with what amplitude. This can be the sole form of informational feedback to the subject, or it may be used in conjunction with conventional tone feedback. In another variation, the toy vehicle may instead be outside the observability of the subject, such as in another room, in which case tone feedback may be the only form of informational feedback provided to the subject. Further, if the subject is well trained, it is entirely feasible and practical to place the output device outside the observability of the subject and provide no informational feedback whatsoever.

Figure 5:
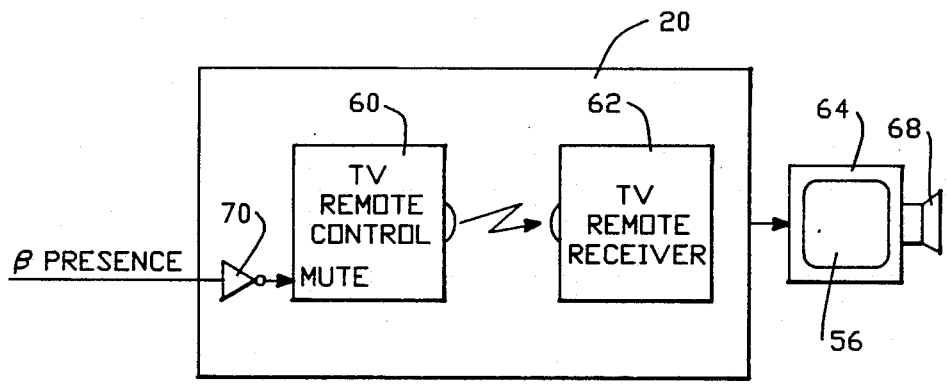

FIG. 5 illustrates the use of the apparatus of FIG. 1 for providing beta training to a subject. Beta training is useful for elderly subjects, for example, since it helps to improve concentration and attention. This can be achieved through the use of EEG biofeedback instrumentation using simple auditory or visual feedback, but the enhancement of the feedback modality shown in FIG. 5 tends to accelerate the learning process by keeping the trainee more attentive to the task. In FIG. 5 the device control block 20 comprises an ordinary TV remote control unit 60 having a mute key, modified as hereinafter described. It also comprises the TV remote receiver portion 62 associated with the television console. The output device 64 is the remainder of the television, including the speaker 68 and the TV screen 66 for displaying a subject's favorite program. The TV remote control unit 60 is modified to receive the beta presence signal from the EEG detector 10a to activate the mute key. Depending on how the actual hookup is made, a signal inverter 70 may be required between the beta presence output of the EEG detector 10a and the modified TV remote control 60.

In operation, the subject sits facing the television 64 and attempts to watch the show. If the subject's mind drifts and the amplitude of beta waves produced falls below the preset threshold, the mute key of the TV remote control 60 is activated and the audio output of the TV 64 turns off. Thus, if the subject wants to Watch his show, he must remain attentive to it.

Figure 6:
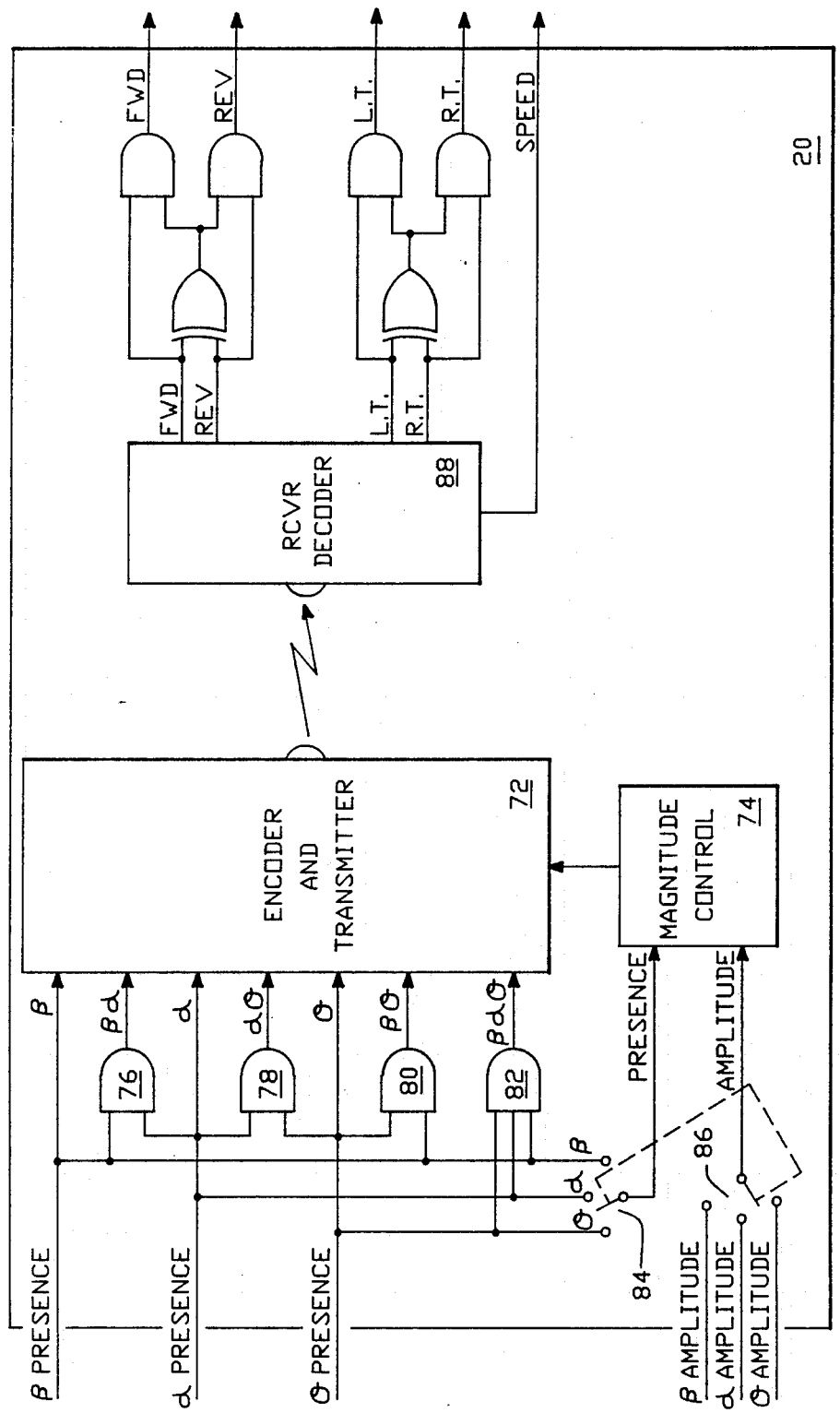

FIG. 6 shows an expansion of the device control block 20 as shown in FIG. 3, in a manner which provides for much greater control of the movement of the toy vehicle 30. Before describing it in detail, it is worthwhile noting that it is entirely possible for a subject to produce brainwave signals which have components in more than one of the defined bands. This can appear as a complex wave having a higher frequency signal superimposed over a lower frequency signal, or, for adjacent bands, it may appear as a waveform having a single major frequency component which is borderline between the two bands. Typically, as a subject moves from beta into alpha, the brainwave pattern reflects a relatively sudden move to a frequency at the high end of alpha, with a small amount of beta superimposed. As the subject settles into alpha, the beta component diminishes while the frequency of the alpha component slowly moves more solidly into the band. A move from alpha production into theta typically occurs as a gradual frequency reduction into the theta band of a signal having only the one major frequency component. A combined beta-alpha state will therefore, typically (but not always) appear as a beta wave superimposed on an alpha wave, whereas a combined alpha-theta state will typically (but not always) appear as a signal having a single major frequency component at approximately the borderline frequency. The states of consciousness associated with either form of multiple band brainwave production are essentially the same, and it is probable that a subject cannot distinguish between them. As will be seen, neither does the apparatus described herein distinguish between them.

It should also be noted that it is difficult, but not impossible, to generate both beta and theta simultaneously as well even though they are not adjacent bands. The brainwave pattern of a subject in beta-theta would appear as beta waves superimposed over theta waves. The state of consciousness reflects a combination of mental activity and detachment with deep relaxation, inner awareness of body sensations, emotions and images.

It is also possible for a subject to generate beta, alpha and theta simultaneously, or to generate a brainwave pattern having no significant component in any of the four bands, beta, alpha, theta or delta. The latter brainwave pattern is referred to herein as "flat." Since it is much more difficult for subjects to learn to produce beta-theta, beta-alpha-theta or flat brainwave patterns, it is preferred to have device control apparatus 20 respond only to the other five permutations (beta, alpha, theta, beta-alpha and alpha-theta). Nevertheless, for illustration purposes, the apparatus shown in FIG. 6 responds to all of the permutations except "flat."

Referring to FIG. 6, there is shown a device control block 20 for use with the invention. It includes an encoder/transmitter 72 similar to the encoder/transmitter 42 in FIG. 3, having one input connected to the output of a magnitude control block 74, similar to the magnitude control block 40 shown in FIG. 3. Other inputs to the encoder/transmitter 72 include the beta presence, alpha presence and theta presence outputs of EEG detector 10a. The beta presence and alpha presence signals are also connected to the input of an AND gate 76, the output of which forms a beta-alpha input to encoder/transmitter 72. The alpha presence signal is also connected to one input of an AND gate 78, the other input of which is connected to the theta presence signal. The output of AND gate 78 forms an alpha-theta input to encoder/transmitter 72. The theta presence signal is also connected to one input of an AND gate 80, the other input of which is connected to the beta presence signal. The output of AND gate 80 forms a beta-theta input to encoder/transmitter 72. The beta, alpha and theta presence signals are also connected to the inputs of a 3-input AND gate 82, the output of which forms a beta-alpha-theta input to encoder/transmitter 72.

The presence input of magnitude control block 74 derives from the common of a 3-position switch 84 capable of selecting either the beta, alpha or theta presence signals. The switch 84 is ganged together with another 3-position switch 86, the common of which is connected to the amplitude input of the magnitude control block 74. The switch 86 selects either the beta, alpha or theta amplitude signal from the EEG detector 10a in correspondence with the selection made by switch 84.

The encoder/transmitter 72 generates an encoded infrared signal indicative of the input signals. As with the device control block 20 shown in FIG. 3, the transmission medium may be changed as desired. The encoded signal is picked up by a receiver/decoder 88, which decodes the signals to provide an FWD output, an REV output, an L.T. (left turn) output, an R.T. (right turn) output, and a speed output. The last of these outputs may be made responsive to the signal deriving from the magnitude control block 74, and the others may be made responsive to any of the other EEG pattern inputs to encoder/transmitter 72.

The FWD, REV, L.T. and R.T. signals pass through some combinational logic designed to prevent logical conflicts, and the signals are transmitted to or directly control the toy vehicle 30 (FIG. 1). The speed signal from receiver/decoder 88 also is transmitted to or directly controls the toy vehicle 30. It should be noted that the logic preceding the encoder/transmitter 72, and the logic following the receiver/decoder 88 may be moved around in the data stream or otherwise adapted to the particular application, the only point being that device control block 20 permits the subject to move the toy vehicle in several different manners depending on which of the available brainwave pattern permutations is exhibited.

As with the apparatus of FIGS. 1, 3 and 4, the apparatus of FIGS. 1 and 6 may be operated with or without a separate form of informational feedback, and the movement of the toy vehicle 30 may or may not additionally provide informational feedback.

As previously mentioned, brainwave patterns that include frequency components in two adjacent bands may appear either as a single component at a borderline frequency or as the two components superimposed on each other. If it appears as two frequency components superimposed on each other, then both presence outputs of EEG detector 10a will be active and the appropriate AND gate 76, 78, 80 or 82 will turn on. The same is true if a single borderline frequency is present, since the filters in the EEG detector 10a (chips $U_1$ and $U_2$ in FIG. 2) are chosen to have overlapping skirts. Thus, in congruence with the mental states experienced by subjects, the apparatus does not distinguish between the two forms in which multiple band brainwave patterns may appear.

Figure 7:
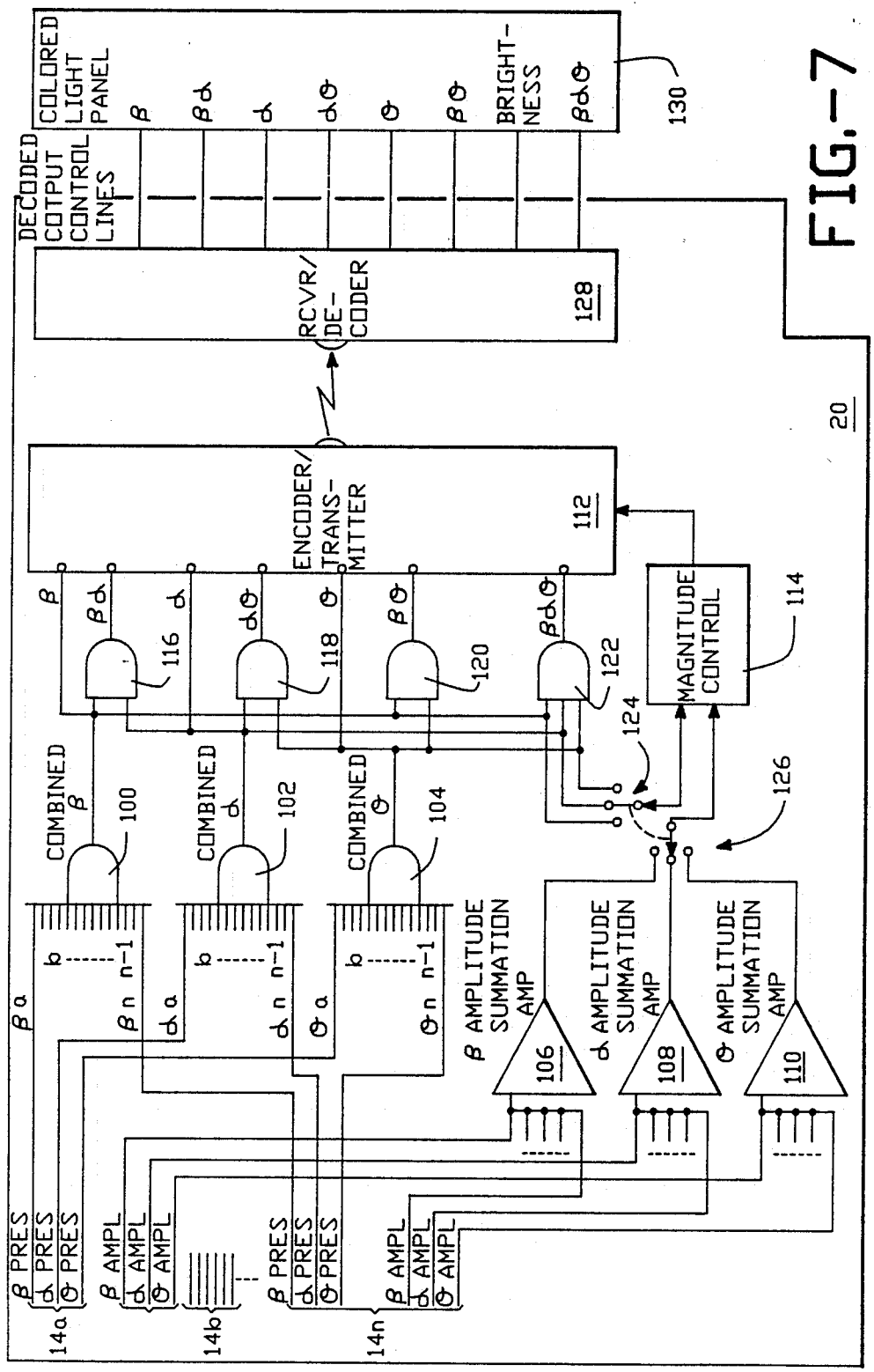

FIG. 7 shows yet another expansion on the inventive concept, in this case for use with two or more subjects. As used herein, the brainwave patterns of two or more subjects are considered "synchronous" when they are at approximately the same frequency (within some predetermined tolerance). They are in "coherence" when they have approximately the same frequency and, further, the peaks of one occur at approximately the same times as the peaks of the other, and the valleys of one occur at approximately the same times as the valleys of the other. Two patterns may be synchronous without being coherent, but they cannot be coherent without being synchronous.

Two or more patterns may also be "simultaneously" within a given band when both have a frequency component somewhere in the band at the same time. They may be at different frequencies within the band, but both are within the band. A pair of brainwave patterns therefore can be simultaneously within a band without being synchronous or coherent, but they cannot be synchronous or coherent without being simultaneously within the band.

Finally, there is a still further condition in which, during some predetermined interval of time, two or more subjects produce brainwave signals within a selected band or combination of bands for at least a predetermined percentage of the interval. Two subjects in such a condition need not even be producing brainwaves in the selected band "simultaneously," since their brainwave patterns may have been within the selected band at different times during the time interval.

The device control apparatus 20 as shown in FIG. 7 may be used for controlling an output device in response to the simultaneity of selected brainwave patterns among a plurality of n subjects. It comprises three n-input AND gates 100, 102 and 104, generating, respectively, a combined beta presence signal, a combined alpha presence signal and a combined theta presence signal. The beta presence signal from each of the EEG detectors 10a–10n is connected to one input of the AND gate 100, while the alpha presence signal from each of the EEG detectors 10a–10n is connected to an input of AND gate 102 and the theta presence signal from each of the EEG detectors 10a–10n is connected to an input of AND gate 104. The output control apparatus 20 further comprises three amplitude summation amplifiers 106, 108 and 110, providing, respectively, combined beta, alpha and theta amplitude signals. The inputs of amplitude summation amp 106 are connected to the beta amplitude signals from all the EEG detectors; the inputs to amplitude summation amplifier 108 are connected to the alpha amplitude outputs of all the EEG detectors; and the inputs to amplitude summation amplifier 110 are connected to the theta outputs from all the EEG detectors.

The remainder of device control apparatus 20 shown in FIG. 7 is similar to that shown in FIG. 6. The presence and amplitude inputs of a magnitude control block 114 similar to magnitude control block 74 in FIG. 6 are connected selectably to the combined beta, alpha and theta presence and amplitude signals, and the output of magnitude control block 114 is connected to an input of an encoder/transmitter 112 similar to the encoder/transmitter 72 in FIG. 6. The combined beta, alpha and theta presence signals are processed by AND gates 116, 118, 120 and 122 similarly to the processing performed by AND gates 76, 78, 80 and 82 in FIG. 6, and provided to the encoder/transmission 112. Again, similarly to FIG. 6, the encoder/transmitter 112 transmits an encoded signal to a receiver/decoder 128, which provides decoded output control lines for controlling the output device 30 (FIG. 1).

The output device for use with the device control apparatus 20 may be a moveable object such as the toy vehicle 30 in FIG. 1, or it may be an informational feedback device such as a colored-light panel 130. The colored-light panel 130 includes different colors or different panels for each of the permutations of brainwave patterns accommodated by the apparatus and the brightness with which these lights will come on depends on the output of the magnitude control apparatus 114. A colored-light panel is chosen since it can provide informational feedback to all of the subjects simultaneously and, if desired, each of the subjects may continue to receive personalized audio feedback signals in headsets controlled by their own respective EEG detector 10a–10n.

In operation, it can be seen that the combined presence signals output from AND gates 100, 102 and 104 will each be active only when all the subjects are simultaneously producing brainwaves within the corresponding band. Since the EEG detectors 10a–10n are the same as those described previously, each subject must individually meet his own threshold and hysteresis requirements before the apparatus will consider that he is producing brainwaves in that band. Thus, all subjects must simultaneously produce a beta signal for the beta-colored light in a colored-light panel 130 to come on. Additionally, the brightness of the appropriate light depends on the sum of the amplitudes in the selected one of the bands being produced by all subjects simultaneously. Thus, for example, if all subjects are producing beta but only weakly, the beta light will come on in colored-light panel 130 but only weakly. The subjects can thereafter modify their mental state to brighten the beta light.

Figure 8:
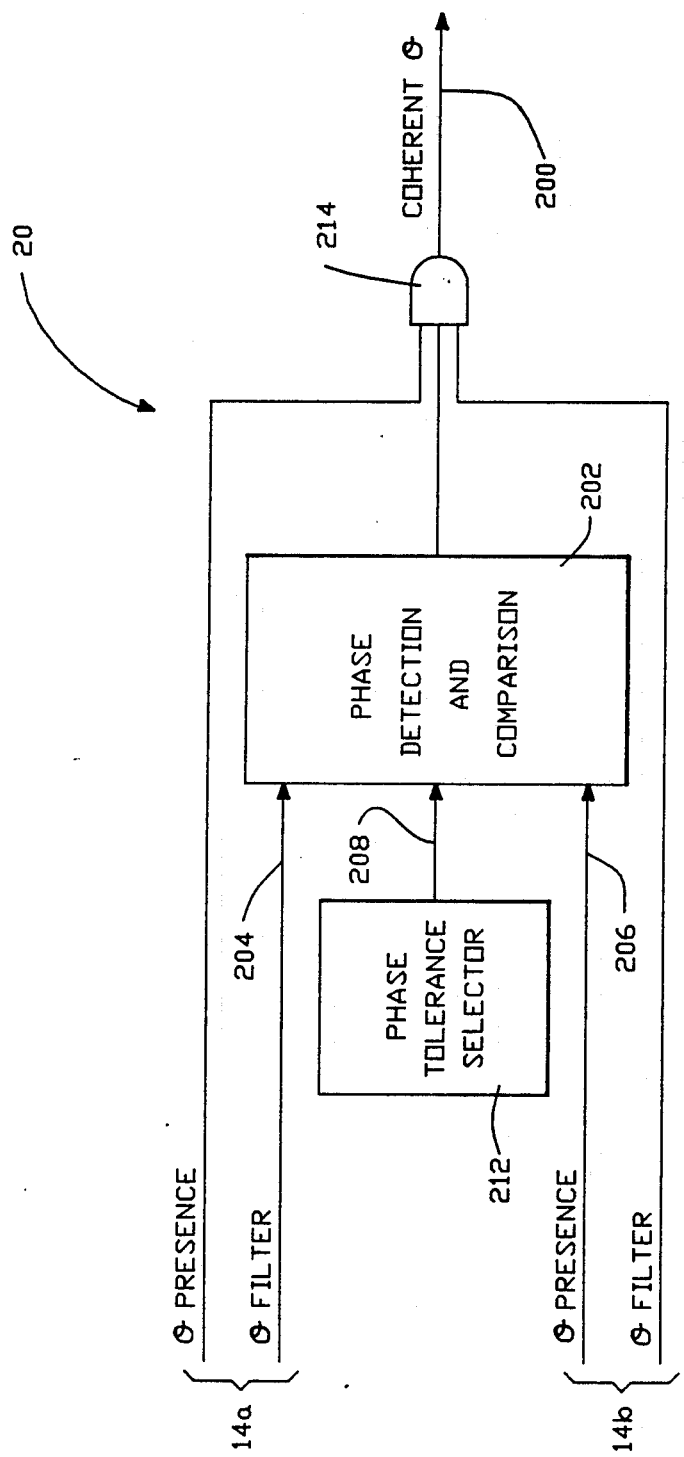

FIG. 8 shows a portion of a device control apparatus 20 which may be used for controlling an output device in response to the "coherence" of selected brainwave patterns among the plurality of subjects. In particular, the portion shown in FIG. 8 generates a coherent theta signal on a line 200 whenever two subjects are producing theta synchronously and within a predetermined phase tolerance. Additional portions would be provided in the device control apparatus 20 for providing a coherent beta signal and a coherent alpha signal, if desired. Alternatively, the portion shown in FIG. 8 may be made switch selectable to select any of the three bands.

The apparatus portion shown in FIG. 8 comprises a phase detection and comparison unit 202, having two signal inputs 204 and 206 and a tolerance selection input 208. The signal input 204 receives the theta filter output of EEG detection apparatus 10a for one subject, and signal input 206 receives the theta filter output of EEG detection apparatus 10b for the second subject. Referring to FIG. 2, these signals may be taken from a respective node 210. The phase tolerance selection input 208 is connected to a phase tolerance selector 212, which may be a hard-wired circuit, a switch, or some other means for providing this signal.

The output of the phase detection and comparison unit 202 is connected to one input of a 3-input AND gate 214. A second input of the AND gate 214 is connected to the theta presence signal from EEG detector 10a, and the third input of AND gate 214 is connected to the theta presence output of EEG detector 10b. The output of AND gate 214 forms the coherent theta output.

In operation, the phase detection and comparison unit 202 subtracts the phase of one of the inputs 204 or 206 from the other, and compares the result to the phase tolerance selection input 208. If the result is less than the phase tolerance selection, the output of phase detection and comparison circuit 202 is activated. Otherwise, it is inactivated.

The coherent theta output on line 200 can be active only when all three of the inputs to AND gate 214 are active. Thus, the coherent theta signal will be active only when both theta presence signals are active and the phase detection and comparison unit 202 indicates coherence. The coherent theta output will therefore be active only when both subjects are in theta and producing theta waves coherently.

Figure 9:
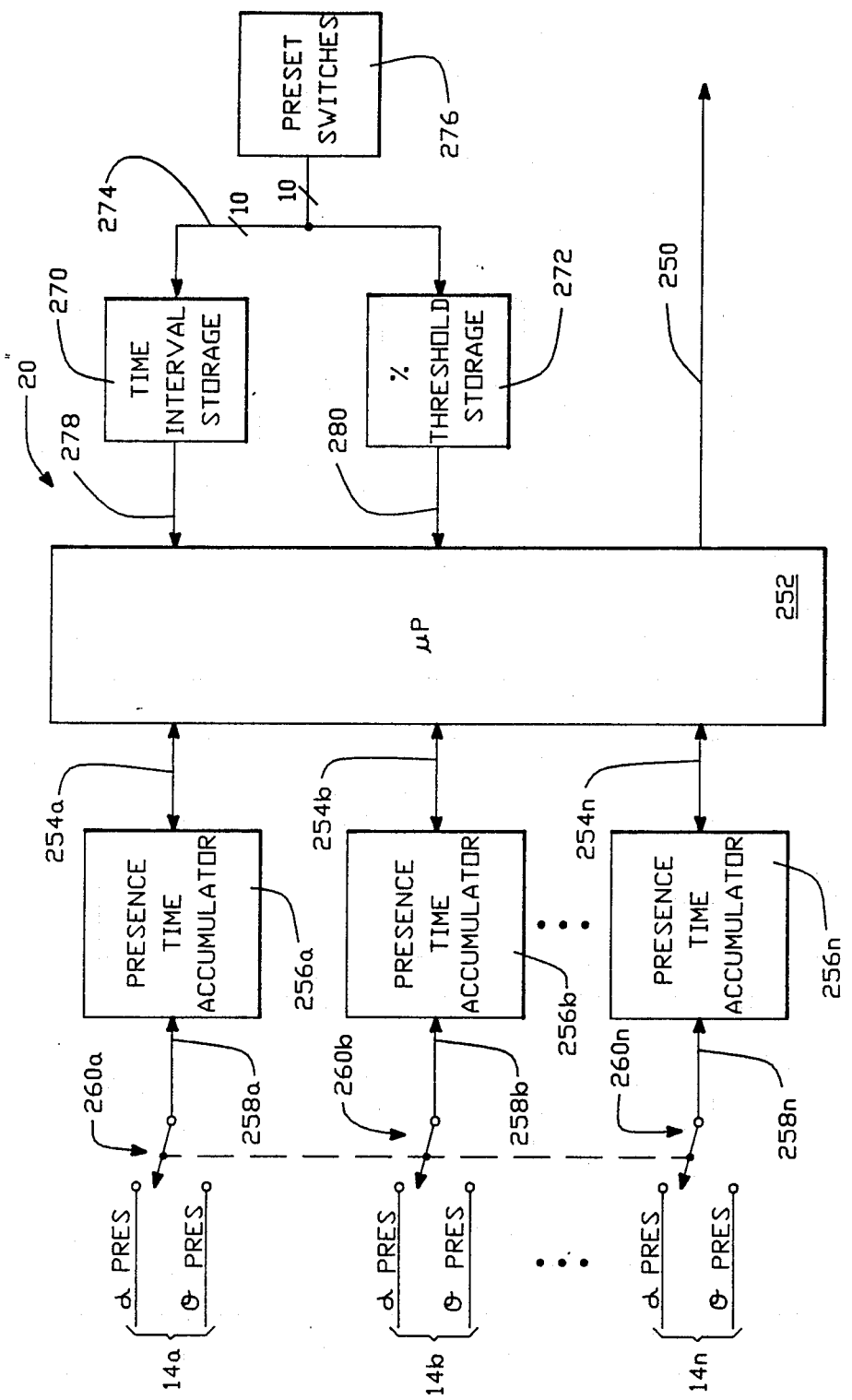

In FIG. 9 there is shown device control apparatus 20 for providing an output signal 250 indicative of whether, during the immediately preceding predetermined interval of time, all the subjects produced brainwaves within a selected band for more than a predetermined percentage of the interval. Though the apparatus may be constructed using discrete components, for variety, the apparatus of FIG. 9 is illustrated using a microprocessor 252. The microprocessor 252 has n I/0 ports 254a-254n, connected, respectively, to n presence time accumulators 256a-256n. Presence time accumulators 256a-256n also have an additional input, 258a-258n, respectively, coupled to the common of respective switches 260a-260n. The switches 260a-260n are ganged together, and each can couple its respective common to either the alpha presence signal or the theta presence signal output from a respective EEG detector 10a-10n. The EEG detectors 10a-10n are, of course, coupled to n subjects. The presence time accumulators 256a-256n are adapted to increment once per second, but only if the corresponding input 258a-258n is active. If the input 258a-258n is inactive, the corresponding presence time accumulator does not change. The current count of the presence time accumulators are available to the microprocessor 252 over the I/0 ports 254a-254n, and the microprocessor 252 can reset each of the presence time accumulators to zero by means not shown.

The device control apparatus as shown in FIG. 9 also includes a time interval storage register 270 and a percent threshold storage register 272. The inputs of these registers 270 and 272 are both connected to a bus 274, which is connected to a set of preset switches 276. The outputs of the registers 270 and 272 are available to the microprocessor 252 via input ports 278 and 280, respectively.

In operation, an operator first presets the time interval over which the study is to take place, by setting the preset switches 276 and activating a control (not shown) for loading them into the time interval storage register 270. Illustratively there are ten preset switches representing ten binary bits, so the operator can set the interval to any period between 1 second and 1,024 seconds (about 17 minutes), inclusive. The operator then uses the preset switches 276 to store a percent threshold, which can be any number from 1% through 100%, in the percent threshold storage register 272. The operator then sets the switches 260a-260n to have the system to either alpha or theta, as desired.

When the study begins, the microprocessor 252 first resets all the presence time accumulators 256a-256n . Assuming the switches 260a-260n have been set to the theta presence poles, the presence time accumulators 256a-256n will begin counting the number of seconds for which each corresponding subject is exhibiting theta. The microprocessor 252 also has an overall time accumulator (not shown) which counts the total number of seconds since the beginning of the interval. When the total time accumulator reaches the number of seconds indicated by the time interval storage register 270, the microprocessor 252 divides the count in the various presence time accumulators 256a-256n by the total number of seconds in the interval to determine the percentage of the interval that each subject was in theta. The microprocessor 252 then compares these percentages with the value in the percent threshold storage register 272, and if all of the values are larger than the value in the percent threshold storage register 272, the microprocessor 252 activates the output line 250. Otherwise, output line 250 is deactivated. The microprocessor 252 then resets the presence time accumulators 256a-256n, and the cycle repeats.

The invention has been described with respect to particular embodiments thereof, and it will be understood that variations which are apparent to a person of ordinary skill are intended to be included within the scope of the claims.

What is claimed is:

1. Brainwave responsive apparatus for use with a subject, comprising;
   an output device; and
   means for controlling said output device to perform a first function in response to the presence or absence in said subject of a brainwave pattern frequency component which is borderline between the alpha and theta ranges of the brainwave spectrum.

2. Brainwave responsive apparatus for use with a subject, comprising:
   an output device; and
   means for controlling said output device to perform a first function in response to the presence or absence in said subject of a brainwave pattern frequency component which is borderline between the beta and alpha ranges of the brainwave spectrum.

3. Brainwave-responsive apparatus for use with a subject, comprising:
   an output device;
   detection apparatus coupleable for sensing the brainwaves of said subject, said detection apparatus having a first presence output indicative of the presence or absence of a frequency component which is borderline between the theta and alpha ranges of the brainwave spectrum; and
   output control apparatus having an input coupleable to said first presence output of said detection apparatus, for causing said output device to perform a first function in response to said first presence output.

4. Brainwave-responsive apparatus according to claim 3, wherein said detection apparatus further has a first amplitude output indicative of the amplitude of the portion of said brainwaves in said borderline range, wherein said first function has a magnitude, and wherein said output control apparatus, when it causes said output device to perform said first function, causes said output device to perform said first function with a magnitude responsive to said first amplitude output.

5. Brainwave-responsive apparatus for use with a subject, comprising:
   an output device;
   detection apparatus coupleable for sensing the brainwaves of said subject, said detection apparatus having a first presence output indicative of the presence or absence of a frequency component which is borderline between the beta and alpha ranges of the brainwave spectrum; and
   output control apparatus having an input coupleable to said first presence output of said detection apparatus, for causing said output device to perform a first function in response to said first presence output.

6. Brainwave-responsive apparatus according to claim 5, wherein said detection apparatus further has a first amplitude output indicative of the amplitude of the portion of said brainwaves in said borderline range, wherein said first function has a magnitude, and wherein said output control apparatus, when it causes said output device to perform said first function, causes said output device to perform said first function with a magnitude responsive to said first amplitude output.

7. Brainwave training apparatus for use with a subject, comprising:
   an EEG detector coupleable to said subject and having a presence output which is active when said subject produces brainwaves within a predetermined band around the theta-alpha borderline frequency and inactive when said subject does not produce brainwaves within said band;
   a moveable object; and
   output control means for causing said moveable object to move when said presence output is active.

8. Apparatus according to claim 7, wherein said EEG detector further has an amplitude output indicative of the amplitude of brainwaves produced by said subject within said band, and wherein said output control means, when it causes said moveable object to move, causes said moveable object to move at a speed responsive to said amplitude output.

9. Brainwave-responsive apparatus for use with a plurality of subjects, comprising;
   an output device;
   a plurality of EEG detectors, each coupleable to a corresponding one of said subjects and each producing a first individual presence signal indicative of whether said corresponding one of said subjects is producing a first predetermined brainwave pattern;
   device control means for controlling said output device to perform a first function in response to a signal responsive to all of said first individual presence signals.

10. Apparatus according to claim 9, further comprising individualized informational feedback means for indicating individually to at least one of said subjects whether said at least one of said subjects is producing said first predetermined brainwave pattern.

11. Apparatus according to claim 9, wherein said first predetermined brainwave pattern is defined by a first predetermined one of the beta, alpha and theta brands of the brainwave frequency spectrum.

12. Apparatus according to claim 11, wherein the first predetermined brainwave pattern is defined by the theta band.

13. Apparatus according to claim 9, wherein each of said first individual presence signals has an active and an inactive state, and wherein said device control means controls said output device to perform said first function if and only if all of said first individual presence signals are active.

14. Apparatus according to claim 13, wherein said device control means comprises:
   first combining means for combining all of said first individual presence signals to produce a first combined presence signal; and
   output control means for controlling said output device to perform said first function in response to said first combined presence signal.

15. Apparatus according to claim 14, wherein each of said EEG detectors further produces a second individual presence signal indicative of whether the corresponding one of said subjects is producing a second predetermined brainwave pattern,
   said apparatus further comprising second combining means for combining all of said second individual presence signals to produce a second combined presence signal,
   and wherein said output control means further controls said output device to perform a second function in response to said second combined presence signal.

16. Apparatus according to claim 14, wherein each of said EEG detectors further produces a second individual presence signal indicative of whether the corresponding one of said subjects is producing a second predetermined brainwave pattern, said apparatus further comprising second combining means for combining all of said second individual presence signals to produce a second combined presence signal, and wherein said output control means further controls said output device to perform a third function in response to the simultaneous activation of both said first and second combined presence signals.

17. Apparatus according to claim 14, wherein each of said EEG detectors further provides a first individual amplitude signal indicative of the amplitude of the portion of the brainwaves of said corresponding one of said subjects, which portion is within the first predetermined brainwave pattern, wherein the first function has a magnitude, and wherein the device control means when it controls said output device to perform said first function, controls said magnitude in response to all of said first individual amplitude signals.

18. Apparatus according to claim 17, wherein said output device comprises a light, wherein said first function comprises turning on said light, and wherein said magnitude is the brightness of said light.

19. Apparatus according to claim 9, wherein said first function provides combined informational feedback to all of said subjects.

20. Apparatus according to claim 9, wherein said first function is a productive function.

21. Apparatus according to claim 9, wherein each of said first individual presence signals has an active and an inactive state, and wherein said device control means controls said output device to perform said first function following a predetermined interval of time only if each of said individual presence signals was active for at least a predetermined percentage of said interval of time.

22. Apparatus according to claim 9, further comprising means for controlling said output device to perform a second function if and only if all of said subjects are producing brainwaves synchronously to within a predetermined tolerance.

23. Apparatus according to claim 9, further comprising means for controlling said output device to perform a second function if and only if all of said subjects are producing brainwaves coherently to within a predetermined tolerance.

24. Brainwave-responsive apparatus for use with a plurality of subjects, comprising:
an output device; and
device control means, responsive to the brainwave patterns of said subjects for controlling said output device to perform a first function whenever all of said subjects simultaneously produce a first predetermined brainwave pattern.

25. Brainwave-responsive apparatus for use with a plurality of subjects, comprising:
an output device; and
device control mean, responsive to the brainwave patterns of said subjects for controlling said output device to perform a first function whenever all of said subjects produce, in a first predetermined brainwave pattern, brainwave signals which are coherent to within a predetermined tolerance.

26. Brainwave-responsive apparatus for use with a plurality of subjects, comprising:
an output device; and
device control means, responsive of the brainwave patterns of said subjects for controlling said output device to perform a first function whenever all of said subjects produce, in a first predetermined brainwave pattern, brainwave signals which are synchronous to within a predetermined tolerance.

27. Brainwave-responsive apparatus for use with a plurality of subjects, comprising:
an output device; and
device control means, responsive of the brainwave pattern of said subjects for controlling said output device to perform a first function whenever, during a predetermined preceding interval of time, each of said subjects produced a first predetermined brainwave pattern for at least a predetermined percentage of said interval.

28. Brainwave-responsive apparatus for use with a plurality of subjects, comprising:
an EEG detector corresponding to each of said subjects, each of said EEG detectors providing a theta presence signal which is active when the corresponding one of said subjects produces theta and inactive when said corresponding one of said subjects does not produce theta;
theta presence combining circuitry having an input coupled to receive each of said theta presence signals and producing a combined theta presence signal which is active when all of said theta presence signals are active and inactive when at least one of said theta presence signals is inactive; and
an output device coupled to receive said combined theta presence signal and adapted to provide informational feedback to all of said subjects indicative of whether said combined theta presence signal is active or inactive.

29. Apparatus according to claim 28, wherein each of said EEG detectors further provides a beta presence signal which is active when the corresponding one of said subjects produces beta and inactive when said corresponding one of said subjects does not produce beta, and an alpha presence signal which is active when said corresponding one of said subjects produces alpha and inactive when said corresponding one of said subjects does not produce alpha, said apparatus further comprising:
beta presence combining circuitry having an input coupled to receive each of said beta presence signals and producing a combined beta presence signal which is active when all of said beta presence signals are active and inactive when at least one of said beta presence signals is inactive; and
alpha presence combining circuitry having an input coupled to receive each of said alpha presence signals and producing a combined alpha presence signal which is active when all of said alpha presence signals are active and inactive when at least one of said alpha presence signals is inactive,
and wherein said output device is further coupled to receive said combined beta presence signal and said combined alpha presence signal, is further adapted to provide informational feedback to all of said subjects indicative of whether said combined beta presence signal is active or inactive, and is further adapted to provide informational feedback to all of said subjects indicative of whether said combined alpha presence signal is active or inactive.

30. Brainwave-responsive apparatus for use with a plurality of subjects, comprising:

an EEG detector corresponding to each of said subjects, each of said EEG detectors providing a theta amplitude signal which indicates the amplitude of any theta waves being produced by the corresponding one of said subjects;

theta amplitude summing circuitry having an input coupled to receive each of said theta amplitude signals and producing a combined theta amplitude signal which is responsive to the sum of all said theta amplitude signals; and an output device coupled to receive said combined theta amplitude signal and adapted to provide informational feedback to all of said subjects indicative of the amplitude of said combined theta amplitude signal.

31. Brainwave responsive apparatus for use with a subject, comprising:
an output device; and
means for controlling said output device to perform a first function in response to the presence or absence in said subject of a brainwave pattern frequency component within a predetermined band around 7.5 Hz.

* * * * *

UNITED STATES PATENT AND TRADEMARK OFFICE
CERTIFICATE OF CORRECTION

PATENT NO. : 4,949,726

DATED : August 21, 1990

INVENTOR(S) : Hartzell et al.

It is certified that error appears in the above-identified patent and that said Letters Patent is hereby corrected as shown below:

```
Column 5, line 25, after "rarely" and before ","
   delete "olean" and insert therefor --clean--.
```

Signed and Sealed this

Seventh Day of January, 1992

Attest:

HARRY F. MANBECK, JR.

Attesting Officer

Commissioner of Patents and Trademarks